United States Patent
Ohbuchi et al.

(10) Patent No.: US 11,300,529 B2
(45) Date of Patent: Apr. 12, 2022

(54) ANALYSIS APPARATUS, ANALYSIS METHOD AND ANALYSIS PROGRAM

(71) Applicant: Rigaku Corporation, Tokyo (JP)

(72) Inventors: Atsushi Ohbuchi, Tokyo (JP); Takayuki Konya, Tokyo (JP); Go Fujinawa, Tokyo (JP); Akihiro Himeda, Tokyo (JP)

(73) Assignee: RIGAKU CORPORATION, Akishima (JP)

( * ) Notice: Subject to any disclaimer, the term of this patent is extended or adjusted under 35 U.S.C. 154(b) by 190 days.

(21) Appl. No.: 16/074,967

(22) PCT Filed: Feb. 15, 2017

(86) PCT No.: PCT/JP2017/005543
§ 371 (c)(1),
(2) Date: Aug. 2, 2018

(87) PCT Pub. No.: WO2017/141973
PCT Pub. Date: Aug. 24, 2017

(65) Prior Publication Data
US 2019/0041342 A1    Feb. 7, 2019

(30) Foreign Application Priority Data
Feb. 17, 2016    (JP) .............................. JP2016-027965

(51) Int. Cl.
*G01N 23/207* (2018.01)
*G01N 23/20* (2018.01)
*G01N 23/223* (2006.01)

(52) U.S. Cl.
CPC ........... *G01N 23/207* (2013.01); *G01N 23/20* (2013.01); *G01N 23/223* (2013.01)

(58) Field of Classification Search
None
See application file for complete search history.

(56) References Cited

U.S. PATENT DOCUMENTS 7,184,517 B2 *  2/2007  Kern ................. G01N 23/2076
                                                       378/90
8,520,802 B2    8/2013  Kern
(Continued)

FOREIGN PATENT DOCUMENTS

JP    2012025635 A  *  2/2012

OTHER PUBLICATIONS

S. Akhmedova et al., "Genetic algorithm based X-ray diffraction analysis for chemical control of aluminium smelters baths," 2015 12th International Conference on Informatics in Control, Automation and Robotics (ICINCO), 2015, pp. 32-39. (Year: 2015).*

(Continued)

*Primary Examiner* — Matthew G Marini
(74) *Attorney, Agent, or Firm* — Birch, Stewart, Kolasch & Birch, LLP

(57) ABSTRACT

An analysis apparatus, an analysis method, and an analysis program by which even unskilled ones can perform quantitative analysis of a composition of high-performance cement with high precision. An analysis apparatus 100 for performing quantitative analysis of components of cement, includes: a content percentage conversion unit 120 for converting content percentages of major elements of a cement sample to content ratios of main crystal phases composing the cement sample by predetermined formulae, the content percentages being obtained as an elemental analysis result; a scale factor estimation unit 140 for estimating initial values of scale factors of Rietveld analysis from the content ratios of main crystal phases obtained in the conversion; and a Rietveld analysis unit 150 for performing Rietveld analysis with respect to an X-ray diffraction measurement result of the cement sample using the initial values of scale factors previously been estimated to calculate (Continued)

content percentages of respective phases of the cement sample.

8 Claims, 5 Drawing Sheets

(56) References Cited

U.S. PATENT DOCUMENTS

| | | |
|---|---|---|
| 8,887,806 B2 | 11/2014 | Iverson et al. |
| 9,851,313 B2* | 12/2017 | Van Den Hoogenhof ................. G01N 23/2206 |
| 2005/0074089 A1 | 4/2005 | Kern |
| 2013/0068140 A1* | 3/2013 | Sawabe ................ C04B 22/066 106/706 |
| 2015/0233846 A1* | 8/2015 | Locklair ............. G01N 23/223 378/45 |

OTHER PUBLICATIONS

European Search Report of EP 17 75 3229.8 dated Oct. 24, 2019.
Jadhav, Rohan, et al., "Computation of X-ray powder diffractograms of cement components and its application to phase analysis and hydration performance of OPC cement", Bull. Mater. Sci., vol. 34, No. 5, Dec. 9, 2011 (Dec. 9, 2011), pp. 1137-1150, XP035030792, ISSN: 0973-7669; DOI: 10.1007/S12034-011-0134-0.

* cited by examiner

| COMPONENT | RIETVELD METHOD ||| (4)BOGUE METHOD (COMPARATIVE EXAMPLE) | STANDARD VALUE |
|---|---|---|---|---|---|
| | (1)CALCULATE SCALE FACTOR FROM FORMULA (EXAMPLE) | (2)SOFTWARE CALCULATES SCALE FACTOR (COMPARATIVE EXAMPLE) | (3)USER ESTIMATES ARBITRARILY SCALE FACTOR (COMPARATIVE EXAMPLE) | | mass% |
| $C_3S$ (Alite) | 64.2 (0.3) | 72.3 (0.5) | 62 (3) | 58.7 | 64.95 ± 1.04 |
| $C_2S$ (Belite) | 18.2 (0.4) | 12.4 (0.7) | 30.3 (1.9) | 20.8 | 17.45 ± 0.96 |
| $C_4AF$ (Ferrite) | 12.30 (0.17) | 11.2 (0.3) | 2.8 (0.4) | 12.4 | 12.20 ± 0.84 |
| $C_3A$ (Aluminate) | 5.26 (0.17) | 4.0 (0.2) | 4.8 (0.4) | 6.1 | 4.99 ± 0.50 |

FIG. 5

ANALYSIS APPARATUS, ANALYSIS METHOD AND ANALYSIS PROGRAM

CROSS REFERENCE TO RELATED APPLICATIONS

This application is from PCT Application No. PCT/JP2017/005543, filed on Feb. 15, 2017, which claims priority to Japanese Application No. P2016-027965, filed on Feb. 17, 2016, the entire contents of which is hereby incorporated by reference.

TECHNICAL FIELD

The present disclosure relates to an analysis apparatus, an analysis method and an analysis program for performing quantitative analysis of components of cement.

BACKGROUND ART

For quality control of cement, it is necessary to analyze a composition of the cement. For that purpose, either the Bogue method, in which calculation is performed from an elemental analysis result, or the Rietveld analysis method, which is a quantitative analysis method of crystal phases, is used (see Patent Literatures 1 and 2). The Bogue method (Bogue R. H., (1929) "Calculation of the compounds in Portland Cement", Ind. Eng. Chem., 1, 192-197) is one of composition analysis methods of cement and was announced by Bogue in 1929. In the Bogue method, the composition of major mineral components is calculated using formulae based on a theory from an elemental analysis result.

The Rietveld method (Rietveld H. M., (1969) "A profile refinement method for nuclear and magnetic structure", J. Applied Cryst., 2, 65-71) is a method of superimposing an actually measured diffraction pattern and a diffraction pattern calculated from crystal structure information, and performing profile fitting to thereby obtain crystal structure information of an actual sample. In the profile fitting, it is possible to calculate a theoretical profile from known crystal structure information and to refine a crystal structure parameter by the least squares method. According to the Rietveld method, even when equal to or more than two crystal phases are contained, quantitative analysis of each phase is possible.

Presently, the Bogue method is frequently used for quality control of cement. However, the Bogue method that uses predetermined formulae is unsuitable for analyzing a composition of various crystal phases. On the other hand, in the Rietveld method, with respect to a scale factor that is one of parameters, a user has to set it or to adjust one that has been set by software. Consequently, an analysis result according to the Rietveld method depends on an initial value, and, therefore, different analysis values are obtained depending on a user. Accordingly, for appropriate analysis, a certain degree of skill is required.

Moreover, there are many reports as analysis examples of cement by the Rietveld analysis. However, in these reports, there is no specific reference to treatment of parameters. In the Rietveld analysis, the analysis method, in particular, the treatment of respective parameters lies in the hands of a user.

SUMMARY

When quantitative analysis of cement components ($C_3S$, $C_2S$, $C_3A$, $C_4AF$) is performed using individually each of the known Bogue method or the Rietveld method, there is such a problem in the analysis by the Bogue method that difference appears between analysis values and actual composition values. In particular, the Bogue method cannot fully cover an analysis of current high-performance cement and analysis by the Rietveld method is required eagerly. However, an analysis value obtained by the Rietveld analysis depends on an initial value of a scale factor for use in the analysis, and, therefore, there is such a problem that a different analyst gives a different result, to degrade the precision of the quantitative value. In particular, for a component included in a small content percentage, this problem appears notably.

The present invention has been done in view of circumstances, and is for providing an analysis apparatus, an analysis method and an analysis program by which even an unskilled person can perform quantitative analysis of composition of high-performance cement with high precision.

(1) In order to accomplish the above-described purpose, the analysis apparatus of the present invention is an analysis apparatus performing quantitative analysis of components of cement, including: a content percentage conversion unit for converting content percentages of major elements of a cement sample to content ratios of main crystal phases composing the cement sample by predetermined formulae, the content percentages being obtained as an elemental analysis result; a scale factor estimation unit for estimating initial values of scale factors of Rietveld analysis from the content ratios of main crystal phases obtained in the conversion; and a Rietveld analysis unit for performing Rietveld analysis with respect to an X-ray diffraction measurement result of the cement sample using the initial values of scale factors having been estimated to calculate content percentages of respective phases of the cement sample.

Hereby, quantitative analysis of components of various types of high-performance cement, which has been difficult by the Bogue formula alone, can be performed with high precision. In addition, with respect to the Rietveld analysis that depends on an initial value, analysis can be performed stably with high precision, without generating difference in results due to degrees of skill of persons. Users do not have to perform trial and error for setting an initial value and the workload is reduced.

(2) Moreover, in the analysis apparatus of the present invention, the main crystal phases are four phases of $C_3S$, $C_2S$, $C_3A$ and $C_4AF$. Hereby, content percentages of main components forming the basis of cement products can be determined efficiently and exact quality control in accordance with the type of cement becomes capable.

(3) Further, in the analysis apparatus of the present invention, the Rietveld analysis unit is for practicing Rietveld analysis while keeping at least crystal structure parameters constant. By assuming crystal structure parameters to be constant in this way, the Rietveld analysis can be performed efficiently.

(4) Furthermore, in the analysis apparatus of the present invention, the predetermined formula is a Bogue formula or a deformed formula based on the Bogue formula. Hereby, content percentages of respective phases of cement can be analyzed stably with high precision.

(5) Still further, in the analysis apparatus of the present invention, the elemental analysis result is a result obtained by X-ray fluorescence analysis of the cement sample. Hereby, the elemental analysis result can be obtained easily and rapidly in a broad range without being influenced by a chemical state.

(6) Still furthermore, in the analysis apparatus of the present invention, the scale factor estimation unit is for specifying an initial value of the scale factor with respect to each of phases previously identified on the basis of the content ratios of main crystal phases obtained by the conversion. Hereby, appropriate setting of the initial value of the scale factor becomes easy, and efficient and highly precise calculation of content percentages becomes capable.

(7) The analysis method of the present invention is an analysis method performing quantitative analysis of components of cement, including the steps of: converting content percentages of major elements in a cement sample to content ratios of main crystal phases composing the cement sample by predetermined formulae, the content percentages being obtained as an elemental analysis result; estimating initial values of scale factors of Rietveld analysis from the content ratios of main crystal phases obtained by the conversion; and performing Rietveld analysis with respect to an X-ray diffraction measurement result of the cement sample using the estimated initial values of scale factors to calculate content percentages of respective phases of the cement sample. Hereby, quantitative analysis of components of various types of high-performance cement can be performed with high precision, irrespective of a degree of skill of a user.

(8) In addition, the analysis program of the present invention is an analysis program performing quantitative analysis of components of cement, including: processing of converting content percentages of major elements in a cement sample to content ratios of main crystal phases composing the cement sample by predetermined formulae, the content percentages being obtained as an elemental analysis result; processing of estimating initial values of scale factors of Rietveld analysis from the content ratios of main crystal phases obtained by the conversion; and processing of performing Rietveld analysis with respect to an X-ray diffraction measurement result of the cement sample using the estimated initial values of scale factors to calculate content percentages of respective phases of the cement sample. Hereby, quantitative analysis of components of various types of high-performance cement can be performed with high precision, irrespective of a degree of skill of a user.

According to the present invention, even when an unskilled person analyses a composition of high-performance cement, quantitative analysis can be performed with high precision.

BRIEF DESCRIPTION OF THE DRAWINGS

FIG. 5 illustrates a table showing analysis results.

DESCRIPTION

Next, embodiments are explained with reference to the drawings. To make the explanation be understood easily, the same reference number is given to the same constituent component in respective drawings, and explanations overlapping with each other are omitted.

Configuration of Analysis Apparatus

Figure 1:
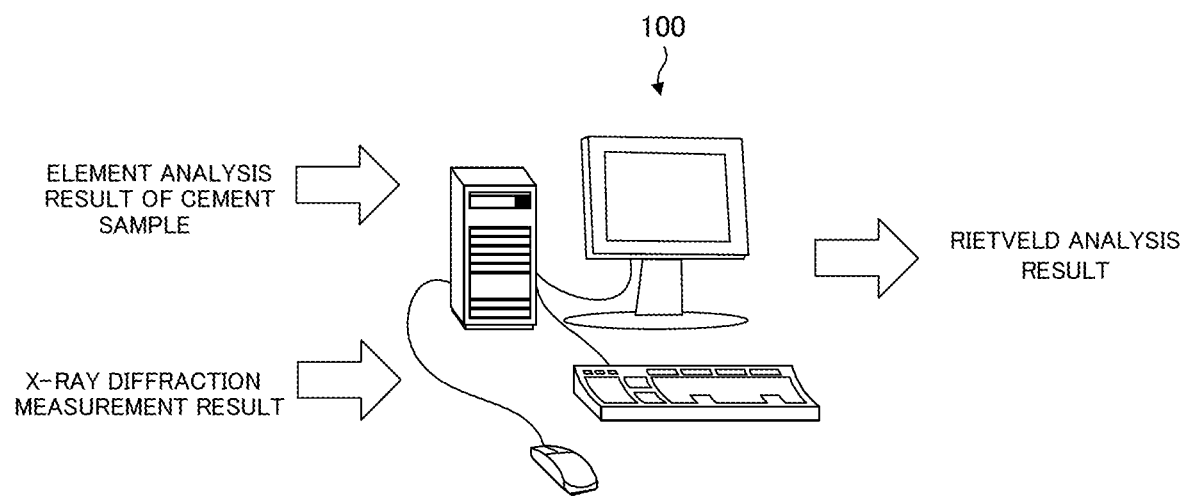
FIG. 1 illustrates a schematic view showing the analysis apparatus of the present invention.

FIG. 1 illustrates a schematic view showing an analysis apparatus 100. The analysis apparatus 100 is, for example, a PC on which an analysis program has been installed, to calculate content percentages of respective components of a cement sample. By performing feedback from the obtained respective components of the cement sample and adjusting an input amount of a raw material, exact quality control of a cement product may be performed.

The analysis apparatus 100 analyzes a cement sample by combining a formula derived on the basis of a theory such as the Bogue formula with the Rietveld analysis. That is, analysis values of respective crystal phases obtained according to formulae are converted to scale factors for use in the Rietveld analysis, while relative values thereof are kept, and these are used as initial values of the analysis. As the result, the scale factor obtained according to the formula is the same irrespective of who the analyst is, and, even when a person not having sufficient knowledge performs the Rietveld analysis, highly quantitative precision can be actualized with respect to cement components.

Figure 2:
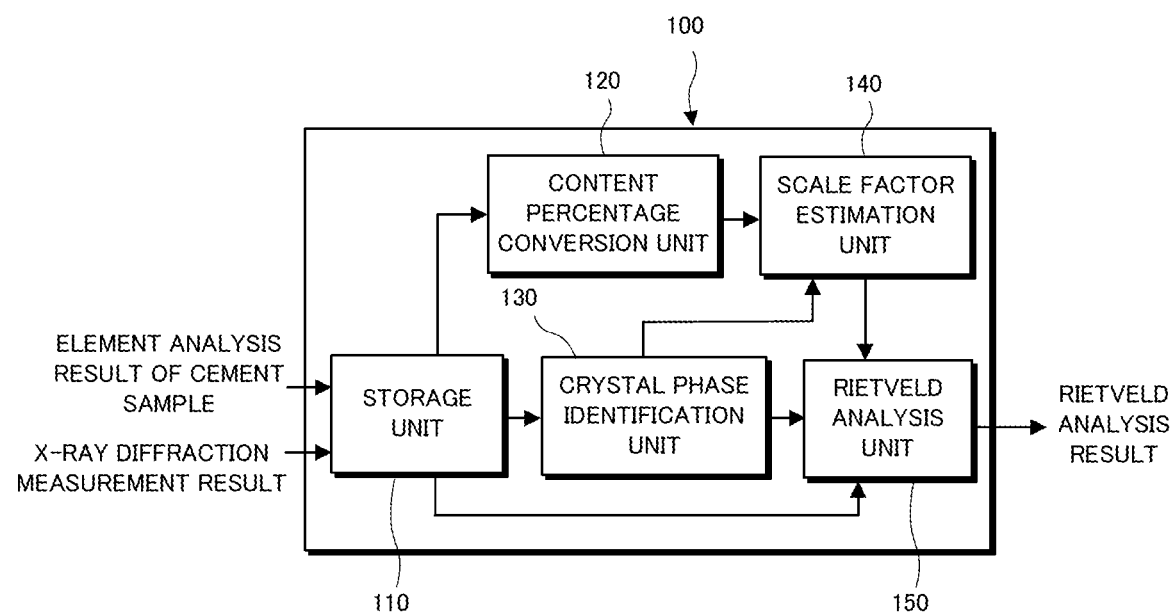
FIG. 2 illustrates a block diagram showing a functional configuration of the analysis apparatus of the present invention.

FIG. 2 illustrates a block diagram showing the functional configuration of the analysis apparatus 100. The analysis apparatus 100 includes a storage unit 110, a content percentage conversion unit 120, a crystal phase identification unit 130, a scale factor estimation unit 140, and a Rietveld analysis unit 150.

The storage unit 110 stores an elemental analysis result and an X-ray diffraction measurement result of a cement sample, having been taken in. The elemental analysis result means content percentages of major elements in the cement sample, which is preferably obtained by X-ray fluorescence analysis. Hereby, the elemental analysis result can be obtained easily and rapidly in a broad range without being influenced by a chemical state. The X-ray diffraction measurement result means a diffraction intensity profile by respective crystal phases.

The content percentage conversion unit 120 converts content percentages of major elements in the cement sample to content ratios of main crystal phases composing the cement sample by prescribed formulae. The prescribed formula is preferably the Bogue formula or Taylor formula that is a deformed formula of the Bogue formula. Hereby, content ratios of respective phases of the cement can be analyzed stably with high precision. Note that, details of the formula are described later.

As the main crystal phases, selection of $C_3S$ (Alite), $C_2S$ (Belite), $C_3A$ (Aluminate) and $C_4AF$ (Ferrite) is preferable, which are major four phases of mineral species. Hereby, content percentages of main components of a cement product can be determined efficiently, which makes it possible to perform exact quality control in accordance with a type of cement.

The crystal phase identification unit 130 identifies crystal phases contained in the cement sample from the X-ray diffraction measurement result. As the result, for example, the above-described major four components and other minor components can be identified.

The scale factor estimation unit 140 estimates an initial value of a scale factor of the Rietveld analysis from each of the content ratios of the main crystal phases having been obtained by the conversion. Hereby, quantitative analysis of components of various types of high-performance cement, which has been difficult according to the Bogue formula alone, can be performed with high precision. Moreover, stable and highly precise analysis can be performed with respect to the Rietveld analysis that depends on the initial value, without generating different results due to degrees of skill of persons. Users do not have to perform trial and error for setting the initial value, and a workload is reduced.

The scale factor estimation unit 140 preferably estimates the initial value of scale factor with respect to the previously identified crystal phase on the basis of the content ratios of the main crystal phases having been obtained by conversion, while keeping content ratios of main crystal phases. Hereby, appropriate setting of the initial value of scale factor becomes easy, which makes highly precise and efficient calculation of content percentages capable. Details of mathematical formulae and processing for use in the estimation are described later.

The Rietveld analysis unit 150 performs the Rietveld analysis with respect to the X-ray diffraction measurement result of the cement sample, using the estimated initial value of scale factor. The Rietveld analysis unit 150 preferably practices the Rietveld analysis, with fixing crystal structure parameters (atomic coordinate, site occupancy rate, atomic displacement parameter). By assuming the crystal structure to be constant in this way, the Rietveld analysis can be performed efficiently. Details of the Rietveld analysis are described later.

Operations of Analysis Apparatus

Figure 3:
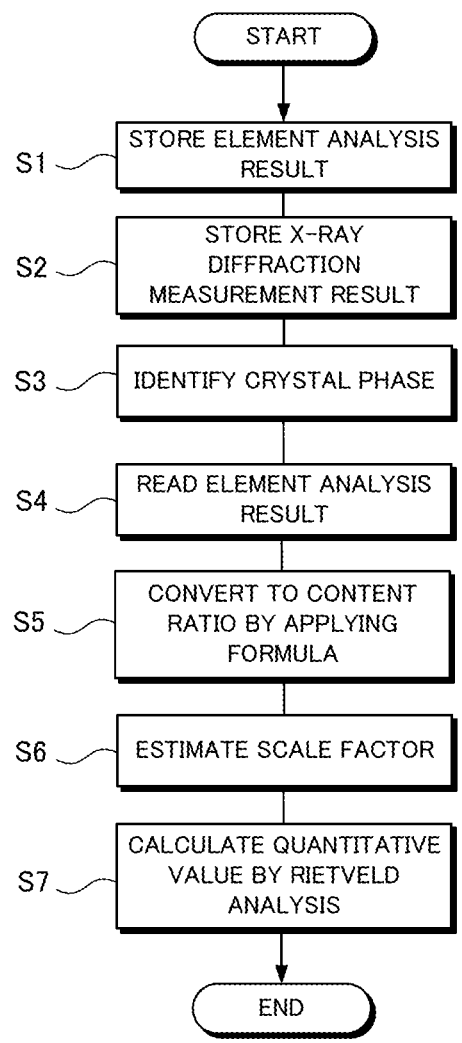
FIG. 3 illustrates a flow chart showing operations of the analysis apparatus of the present invention.

Next, operations of the analysis apparatus 100 configured as described above are explained. FIG. 3 illustrates a flow chart showing operation of the analysis apparatus 100. First, the analysis apparatus 100 takes in and stores the elemental analysis result (Step S1). The elemental analysis result is obtained as content percentages of elements of the cement sample, which can be obtained by X-ray fluorescence analysis. The elemental analysis result is obtained, for example, as a CSV file, which is easily utilized as data. On the other hand, the analysis apparatus 100 takes in and stores an X-ray diffraction measurement result (Step S2). The X-ray diffraction measurement result is, for example, a diffraction intensity profile obtained from a powder sample.

Next, the diffraction intensity profile is read, and, from peak positions thereof, crystal phases of the cement sample are identified (Step S3). Subsequently, the elemental analysis result is read (Step S4), to which predetermined formulae are applied to convert content percentages of major elements in the cement sample to content ratios of major crystal phases (Step S5).

For example, quantitative values of respective crystal phases can be calculated, following the Bogue formulae below. Each of the formulae represents the composition with compounds represented by respective chemical formulae of major crystal phases.

$C_3S = 4.07 \times CaO - (7.60 \times SiO_2 + 6.72 \times Al_2O_3 + 1.43 \times Fe_2O_3 + 2.85 \times SO_3)$ $C_2S = 2.87 \times SiO_2 - 0.754 \times C_3S$ $C_3A = 2.65 \times Al_2O_3 - 1.69 \times Fe_2O_3$ $C_4AF = 3.04 \times Fe_2O_3$ In place of the Bogue formulae, Taylor formulae (deformed Bogue formulae) shown below can also be used.

$C_3S = 4.641200 \times CaO - 8.838681 \times SiO_2 - 7.094597 \times Al_2O_3 - 1.554488 \times Fe_2O_3$ $C_2S = -3.724144 \times CaO + 10.29531 \times SiO_2 + 5.343733 \times Al_2O_3 + 1.065700 \times Fe_2O_3$ $C_3A = 0.117872 \times CaO - 0.369269 \times SiO_2 + 3.669829 \times Al_2O_3 - 3.955085 \times Fe_2O_3$ $C_4AF = -0.023283 \times CaO - 0.055816 \times SiO_2 - 0.867256 \times Al_2O_3 + 5.621492 \times Fe_2O_3$ From content ratios of main crystal phases obtained by the conversion in this way, initial values of scale factors of the Rietveld analysis are estimated (Step S6). For example, a scale factor s can be determined using the following formula.

$W_i = s_i Z_i M_i V_i / \Sigma s_n Z_n M_n V_n$

W: a mass fraction of a crystal phase
s: a scale factor
Z: the number of molecules within a unit cell
M: molecular weight
V: the volume of a unit cell
i: an i-th crystal phase Note that, even in a case where structure information is not known, a content percentage of a crystal phase can be determined when an RIR value is given. The RIR value is an abbreviation of a Reference Intensity Ratio, and is an intensity ratio when a sample to be tested and aluminum oxide are mixed in the equivalent amount. By using the RIR value, content percentages of respective crystal phases in cement may be calculated even when a crystal structure is unidentified.

Subsequently, the Rietveld analysis is performed with respect to the X-ray diffraction measurement result of the cement sample using the estimated initial value of the scale factor, to calculate quantitative values (Step S7). For example, a calculation profile of a following formula can be fitted for the measurement profile.

Figure 4:
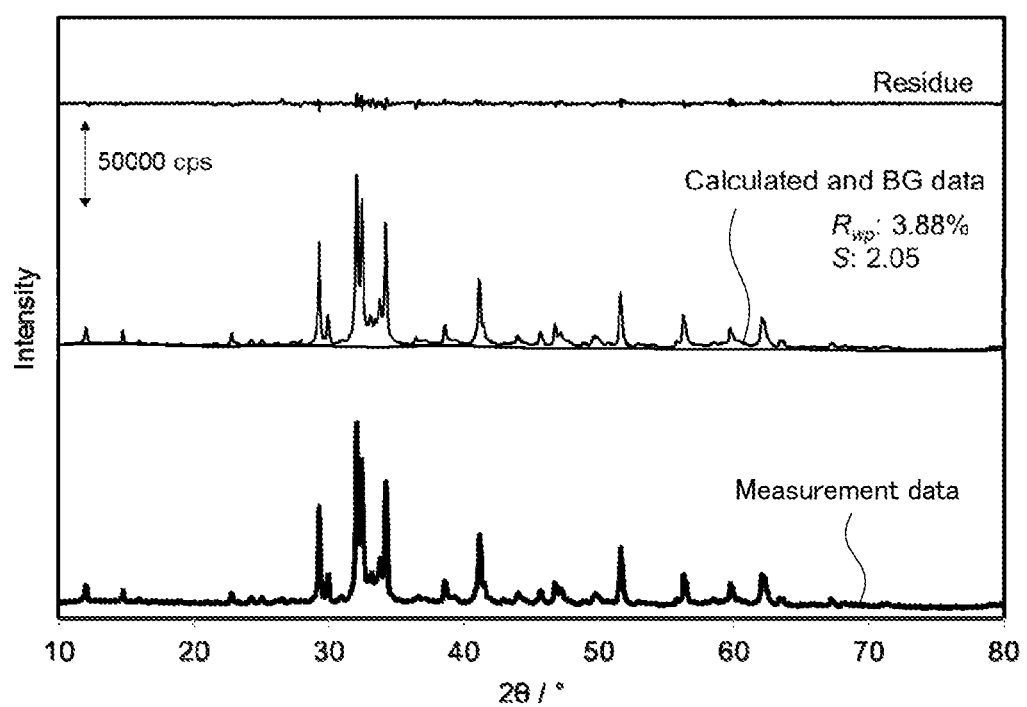
FIG. 4 illustrates a view showing a profile fitting example in the Rietveld analysis.

$y_i^{cal} = A(2\theta_i) \Sigma s_n \Sigma P_{n,h} I_{n,h} \varphi_n (2\theta_i - 2\theta_h - T(2\theta_i)) + y_b(2\theta_i)$ $s_n$: a scale factor
$2\theta_h$: a Bragg angle
$A(2\theta_i)$: intensity correction of absorption, irradiation area
$P_{n,h}$: orientation correction
$I_{n,h}$: integrated intensity
$\varphi_n$: profile function
$T(2\theta_i)$: angle correction
$y_b(2\theta_i)$: background function
n: sum with respect to respective crystal phases
h: sum with respect to Miller index FIG. 4 illustrates a view showing a profile fitting example in the Rietveld analysis. In the example shown in FIG. 4, the NIST2688 standard sample is set as an analysis object. In the example shown in FIG. 4, Rwp, which is the most general R factor in the Rietveld analysis, is 3.88%. Rwp shows weighted degree of concordance including background. On one hand, S is 2.05. When a statistically expected ideal limit value of Rwp is represented by Re, S is defined by Rwp/Re, and, when S=1, it means that refinement is perfect. In the profile fitting in the Rietveld analysis, fitting up to this degree is performed.

As described above, by applying the scale factor having been estimated using a predetermined formula to the Rietveld analysis of cement, a sufficiently converged analysis result can be obtained without estimation of the initial value of the scale factor by a user. Further, with respect to a component having a small content percentage, too, an analysis result having high precision can be obtained, irrespective of who is the user.

Above described operations are performed by executing a program on the analysis apparatus 100. Specifically, a formula for use in cement analysis may be incorporated in X-ray diffraction software, content ratios of respective crystal phases in a cement sample may be determined from an elemental analysis result having been read according to the formula, and the content ratios may be converted to scale factors of the Rietveld analysis, which may be used as initial values of the Rietveld analysis.

EXAMPLES

Using the above-described analysis apparatus 100, actually a cement sample of Portland cement was analyzed. For a same cement sample, X-ray fluorescence analysis and X-ray diffraction measurement were performed. Then, with respect to an obtained elemental analysis result and X-ray diffraction measurement result, each of following (1)-(4), that is, (1) Rietveld analysis using an initial value obtained from the Bogue formula, (2) Rietveld analysis on the basis of an initial value set by software, (3) Rietveld analysis on the basis of an initial value set by a user, and (4) analysis by the Bogue formula alone, was performed to determine corresponding content percentages of crystal phases.

FIG. 5 illustrates a table showing analysis results. An obtained analysis result nearer to the standard value represents higher precision of the analysis. As shown in FIG. 5, in the analysis in the above-described (1), quantitative precision of ordinary ±2% or less for respective crystal phases is accomplished with respect to any component. In contrast, analysis results in (2)-(4), at least one component deviates largely from the standard value. As described above, it has been proved that results with sufficient precision are obtained in the analysis method of the present invention.

The invention claimed is:

1. An analysis apparatus for performing quantitative analysis of components of cement, the analysis apparatus comprising at least one processor configured to:
receive an elemental analysis result of cement sample, which is different from an X-ray diffraction measurement result, and store the received elemental analysis result;
receive the X-ray diffraction measurement result and store the received X-ray diffraction measurement result;
convert content percentages of major elements of a cement sample to content ratios of main crystal phases composing the cement sample by predetermined formulae, the content percentages being obtained from the elemental analysis result;
execute an algorithm to estimate initial values of scale factors of Rietveld analysis based on a correlation between a content ratio of each crystal phase obtained in the conversion, which is the weight ratio of each main crystal phase, and the scale factor ratio of each main crystal phase;
perform Rietveld analysis with respect to the X-ray diffraction measurement result of the cement sample using the initial values of scale factors having been estimated to calculate content percentages of respective phases of the cement sample; and
output the content percentages as the Rietveld analysis result.

2. The analysis apparatus according to claim 1, wherein the main crystal phases are four phases of C3S, C2S, C3A and C4AF.

3. The analysis apparatus according to claim 1, wherein the performing step executes Rietveld analysis with keeping at least crystal structure parameters constant.

4. The analysis apparatus according to claim 1, wherein the predetermined formula is a Bogue formula or a deformed formula based on the Bogue formula.

5. The analysis apparatus according to claim 1, wherein the elemental analysis result is a result obtained by X-ray fluorescence analysis of the cement sample.

6. The analysis apparatus according to claim 1, wherein the estimating step specifies an initial value of the scale factor with respect to each of phases previously identified on the basis of the content ratios of main crystal phases obtained by the conversion.

7. An analysis method for performing quantitative analysis of components of cement, comprising the steps of:
receiving an elemental analysis result of cement sample, which is different from an X-ray diffraction result, and storing the received elemental analysis result;
receiving the X-ray diffraction measurement result and storing the received X-ray diffraction measurement result;
converting content percentages of major elements in a cement sample to content ratios of main crystal phases composing the cement sample by predetermined formulae, the content percentages being obtained from the elemental analysis result;
executing an algorithm to estimate initial values of scale factors of Rietveld analysis based on a correlation between a content ratio of each crystal phase obtained by the conversion, which is the weight ratio of each main crystal phase, and the scale factor ratio of each main crystal phase;
performing Rietveld analysis with respect to the X-ray diffraction measurement result of the cement sample using the estimated initial values of scale factors to calculate content percentages of respective phases of the cement sample; and
outputting the content percentages as the Rietveld analysis result.

8. A non-transitory computer readable recording medium having recorded thereon an analysis program for performing quantitative analysis of components of cement, the analysis program comprising:
receiving an elemental analysis result of cement sample, which is different from an X-ray diffraction result, and storing an elemental analysis result;
receiving the X-ray diffraction measurement result and storing the received X-ray diffraction measurement result;
processing of converting content percentages of major elements in a cement sample to content ratios of main crystal phases composing the cement sample by predetermined formulae, the content percentages being obtained from the elemental analysis result;
executing an algorithm to estimate initial values of scale factors of Rietveld analysis based on a correlation between a content ratio of each crustal phase obtained by the conversion, which is the weight ratio of each main crystal phase, and the scale factor ratio of each main crystal phase;
processing of performing Rietveld analysis with respect to the X-ray diffraction measurement result of the cement sample using the estimated initial values of scale factors to calculate content percentages of respective phases of the cement sample; and
outputting the content percentages as the Rietveld analysis result.

* * * * *